(12) United States Patent
Davis et al.

(10) Patent No.: US 11,793,238 B2
(45) Date of Patent: *Oct. 24, 2023

(54) MICROTEXTURED LIQUID TRANSPORT ELEMENT FOR AEROSOL DELIVERY DEVICE

(71) Applicant: RAI Strategic Holdings, Inc., Winston-Salem, NC (US)

(72) Inventors: Michael F. Davis, Clemmons, NC (US); Frederic Philippe Ampolini, Winston-Salem, NC (US); James William Rogers, Cornelius, NC (US); Andries Don Sebastian, Clemmons, NC (US); Eric Taylor Hunt, Pfafftown, NC (US); Sawyer Hubbard, Winston-Salem, NC (US); David Allan Brammer, Smyrna, GA (US)

(73) Assignee: RAI Strategic Holdings, Inc., Winston-Salem, NC (US)

( * ) Notice: Subject to any disclaimer, the term of this patent is extended or adjusted under 35 U.S.C. 154(b) by 351 days.

This patent is subject to a terminal disclaimer.

(21) Appl. No.: 17/021,077

(22) Filed: Sep. 15, 2020

(65) Prior Publication Data

US 2020/0404970 A1 Dec. 31, 2020

Related U.S. Application Data

(63) Continuation of application No. 15/679,849, filed on Aug. 17, 2017, now Pat. No. 10,791,761.

(51) Int. Cl.
*A24F 40/46* (2020.01)
*H05B 3/22* (2006.01)
(Continued)

(52) U.S. Cl.
CPC .............. *A24F 40/46* (2020.01); *A24F 40/44* (2020.01); *A24F 40/10* (2020.01);
(Continued)

(58) Field of Classification Search
CPC .......... A24F 40/10; A24F 40/44; A24F 40/46; A61M 2205/3653; H05B 2203/01; H05B 2203/016; H05B 2203/021; H05B 3/22
(Continued)

(56) References Cited

U.S. PATENT DOCUMENTS

| 4,078,525 A | 3/1978 | Chiba |
| 4,414,037 A | 11/1983 | Friedheim |

(Continued)

FOREIGN PATENT DOCUMENTS

| RU | 2608298 C2 | 1/2017 |
| UA | 67598 U | 2/2012 |

(Continued)

OTHER PUBLICATIONS

Lee, et al., "Artificial Lotus Leaf Structures Made By Blasting With Sodium Bicarbonate," Current Applied Physics, May 2011, vol. 11(3), pp. 800-804.

(Continued)

*Primary Examiner* — Sang Y Paik
(74) *Attorney, Agent, or Firm* — Womble Bond Dickinson (US) LLP

(57) ABSTRACT

The present disclosure relates to aerosol delivery devices. The aerosol delivery devices may include a reservoir containing a liquid aerosol precursor composition and an atomizer including an electrical resistance heating element and a nonfibrous liquid transport element having a microtextured surface adapted for surface wicking of the liquid aerosol precursor composition across the microtextured surface, the microtextured surface of the liquid transport element being (Continued)

Figure 1:
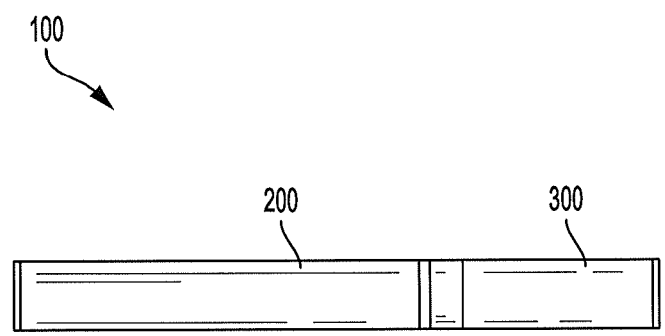

in fluid communication with the reservoir and in fluid communication with the electric resistance heating element.

14 Claims, 12 Drawing Sheets

(51) Int. Cl.
  *A24F 40/44* (2020.01)
  *A24F 40/10* (2020.01)
(52) U.S. Cl.
  CPC ....... *A61M 2205/3653* (2013.01); *H05B 3/22* (2013.01); *H05B 2203/01* (2013.01); *H05B 2203/016* (2013.01); *H05B 2203/021* (2013.01)
(58) Field of Classification Search
  USPC ........................................................ 392/404
  See application file for complete search history.

(56) References Cited

U.S. PATENT DOCUMENTS

| | | | |
|---|---|---|---|
| 4,639,368 A | 1/1987 | Niazi et al. | |
| 4,733,056 A * | 3/1988 | Kojima | H05B 3/283 219/544 |
| 4,735,217 A | 4/1988 | Gerth et al. | |
| 4,922,901 A | 5/1990 | Brooks et al. | |
| 4,947,874 A | 8/1990 | Brooks et al. | |
| 4,947,875 A | 8/1990 | Brooks et al. | |
| 5,060,671 A | 10/1991 | Counts et al. | |
| 5,093,894 A | 3/1992 | Deevi et al. | |
| 5,154,192 A | 10/1992 | Sprinkel et al. | |
| 5,178,878 A | 1/1993 | Welding et al. | |
| 5,223,264 A | 6/1993 | Welding et al. | |
| 5,224,498 A | 7/1993 | Deevi et al. | |
| 5,228,460 A | 7/1993 | Sprinkel et al. | |
| 5,249,586 A | 10/1993 | Morgan et al. | |
| 5,261,424 A | 11/1993 | Sprinkel, Jr. | |
| 5,322,075 A | 6/1994 | Deevi et al. | |
| 5,353,813 A | 10/1994 | Deevi et al. | |
| 5,372,148 A | 12/1994 | McCafferty et al. | |
| 5,388,594 A | 2/1995 | Counts et al. | |
| 5,468,936 A | 11/1995 | Deevi et al. | |
| 5,498,850 A | 3/1996 | Das | |
| 5,498,855 A | 3/1996 | Deevi et al. | |
| 5,522,008 A | 5/1996 | Bernard | |
| 5,530,225 A | 6/1996 | Hajaligol | |
| 5,573,692 A | 11/1996 | Das et al. | |
| 5,591,368 A | 1/1997 | Fleischhauer et al. | |
| 5,659,656 A | 8/1997 | Das | |
| 5,665,262 A | 9/1997 | Hajaligol et al. | |
| 5,666,977 A | 9/1997 | Higgins et al. | |
| 5,934,289 A | 8/1999 | Watkins et al. | |
| 5,954,979 A | 9/1999 | Counts et al. | |
| 5,967,148 A | 10/1999 | Harris et al. | |
| 6,040,560 A | 3/2000 | Fleischhauer et al. | |
| 6,053,176 A | 4/2000 | Adams et al. | |
| 6,164,287 A | 12/2000 | White | |
| 6,196,218 B1 | 3/2001 | Voges | |
| 6,772,756 B2 | 8/2004 | Shayan | |
| 6,803,545 B2 | 10/2004 | Blake et al. | |
| 6,810,883 B2 | 11/2004 | Felter et al. | |
| 6,854,461 B2 | 2/2005 | Nichols et al. | |
| 6,974,590 B2 | 12/2005 | Pather et al. | |
| 7,040,314 B2 | 5/2006 | Nguyen et al. | |
| 7,293,565 B2 | 11/2007 | Griffin et al. | |
| 7,381,667 B2 | 6/2008 | Bergquist et al. | |
| 7,513,253 B2 | 4/2009 | Kobayashi et al. | |
| 7,726,320 B2 | 6/2010 | Robinson et al. | |
| 7,832,410 B2 | 11/2010 | Hon | |
| 7,896,006 B2 | 3/2011 | Hamano et al. | |
| 8,079,371 B2 | 12/2011 | Robinson et al. | |
| 8,156,944 B2 | 4/2012 | Han | |
| 8,205,622 B2 | 6/2012 | Pan | |
| 8,375,957 B2 | 2/2013 | Hon | |
| 8,402,976 B2 | 3/2013 | Fernando et al. | |
| 8,424,541 B2 | 4/2013 | Crawford et al. | |
| 8,627,828 B2 | 1/2014 | Strickland et al. | |
| 8,689,804 B2 | 4/2014 | Fernando et al. | |
| 8,794,231 B2 | 8/2014 | Thorens et al. | |
| 8,851,083 B2 | 10/2014 | Oglesby et al. | |
| 8,881,737 B2 | 11/2014 | Collett et al. | |
| 8,910,639 B2 | 12/2014 | Chang et al. | |
| 8,915,254 B2 | 12/2014 | Monsees et al. | |
| 8,925,555 B2 | 1/2015 | Monsees et al. | |
| 9,220,302 B2 | 12/2015 | DePiano et al. | |
| 9,254,002 B2 | 2/2016 | Chong et al. | |
| 10,791,761 B2 * | 10/2020 | Davis | A24F 40/46 |
| 2006/0196518 A1 | 9/2006 | Hon | |
| 2009/0107635 A1 * | 4/2009 | Kano | H05B 3/143 118/620 |
| 2009/0188490 A1 | 7/2009 | Han | |
| 2010/0018539 A1 | 1/2010 | Brinkley et al. | |
| 2010/0024834 A1 | 2/2010 | Oglesby et al. | |
| 2010/0028766 A1 | 2/2010 | Peckerar et al. | |
| 2010/0170522 A1 | 7/2010 | Sun et al. | |
| 2010/0307518 A1 | 12/2010 | Wang | |
| 2012/0055494 A1 | 3/2012 | Hunt et al. | |
| 2013/0008457 A1 | 1/2013 | Zheng et al. | |
| 2013/0192615 A1 | 8/2013 | Tucker et al. | |
| 2013/0255702 A1 | 10/2013 | Griffith, Jr. et al. | |
| 2014/0000638 A1 | 1/2014 | Sebastian et al. | |
| 2014/0060554 A1 | 3/2014 | Collett et al. | |
| 2014/0096781 A1 | 4/2014 | Sears et al. | |
| 2014/0096782 A1 | 4/2014 | Ampolini et al. | |
| 2014/0261495 A1 | 9/2014 | Novak, III et al. | |
| 2014/0270727 A1 | 9/2014 | Ampolini et al. | |
| 2015/0020823 A1 | 1/2015 | Lipowicz et al. | |
| 2015/0020830 A1 | 1/2015 | Koller | |
| 2015/0059780 A1 | 3/2015 | Davis et al. | |
| 2015/0090279 A1 | 4/2015 | Chen | |
| 2015/0335071 A1 | 11/2015 | Brinkley et al. | |
| 2016/0007652 A1 | 1/2016 | Taluskie et al. | |
| 2016/0015926 A1 | 1/2016 | Hermez et al. | |
| 2018/0020722 A1 | 1/2018 | Davis et al. | |
| 2018/0020723 A1 | 1/2018 | Davis et al. | |

FOREIGN PATENT DOCUMENTS

| | | |
|---|---|---|
| WO | WO 97/06786 | 2/1997 |
| WO | WO 2010/003480 | 1/2010 |
| WO | WO 2010/091593 | 8/2010 |
| WO | WO 2013/089551 | 6/2013 |
| WO | WO 2014/182736 | 11/2014 |
| WO | WO 2015/066127 | 5/2015 |
| WO | WO 2015/117701 | 8/2015 |
| WO | WO 2015/153443 | 10/2015 |
| WO | WO 2015/186000 | 12/2015 |
| WO | WO 2015/189623 | 12/2015 |
| WO | WO 2016/007516 | 1/2016 |

OTHER PUBLICATIONS

Korean Notice of Allowance dated Jul. 2, 2023, in corresponding Korean application No. 2020-7007683.
Ukraine Notice of Allowance dated Jun. 13, 2023, in corresponding Ukrainian application No. a 2020 01032.

* cited by examiner

MICROTEXTURED LIQUID TRANSPORT ELEMENT FOR AEROSOL DELIVERY DEVICE

CROSS-REFERENCE TO RELATED APPLICATIONS

This application is a continuation of U.S. application Ser. No. 15/679,849, filed Aug. 17, 2017, which application is hereby incorporated by reference in its entirety in this application.

BACKGROUND

Field of the Disclosure

The present disclosure relates to aerosol delivery devices such as electronic cigarettes, and more particularly to aerosol delivery devices including an atomizer. The atomizer may be configured to heat an aerosol precursor composition, which may be made or derived from tobacco or otherwise incorporate tobacco, to form an inhalable substance for human consumption.

Description of Related Art

Many devices have been proposed through the years as improvements upon, or alternatives to, smoking products that require combusting tobacco for use. Many of those devices purportedly have been designed to provide the sensations associated with cigarette, cigar, or pipe smoking, but without delivering considerable quantities of incomplete combustion and pyrolysis products that result from the burning of tobacco. To this end, there have been proposed numerous alternative smoking products, flavor generators, and medicinal inhalers that utilize electrical energy to vaporize or heat a volatile material, or attempt to provide the sensations of cigarette, cigar, or pipe smoking without burning tobacco to a significant degree. See, for example, the various alternative smoking articles, aerosol delivery devices and heat generating sources set forth in the background art described in U.S. Pat. No. 8,881,737 to Collett et al., U.S. Pat. App. Pub. No. 2013/0255702 to Griffith Jr. et al., U.S. Pat. App. Pub. No. 2014/0000638 to Sebastian et al., U.S. Pat. App. Pub. No. 2014/0096781 to Sears et al., U.S. Pat. App. Pub. No. 2014/0096782 to Ampolini et al., and U.S. Pat. App. Pub. No. 2015/0059780 to Davis et al., which are incorporated herein by reference in their entireties. See also, for example, the various embodiments of products and heating configurations described in the background sections of U.S. Pat. No. 5,388,594 to Counts et al. and U.S. Pat. No. 8,079,371 to Robinson et al., which are incorporated by reference in their entireties.

Many electronic cigarette products comprise an atomizer with a "wick/coil" design, which includes an electrical resistance heater wire wrapped around a fibrous wicking material. Such a design has several potential drawbacks, including heating inefficiency, non-homogeneous wicking of liquid components, non-uniform heating or vaporization of liquid components, the presence of heat sinks, and non-optimal aerodynamics. In addition, the wick/coil design may lead to pyrolysis and/or deposition of char at the wick and coil interface. Some of these potential drawbacks can cause a negative sensory impact over time that may limit how long the device can be operated before the atomizer needs replacement.

There remains a need in the art for new atomizer configurations that can improve upon one or more characteristics of an aerosol delivery device, such as uniformity of heating or vaporization, heating efficiency, reduction of charring/pyrolysis, and the like.

BRIEF SUMMARY OF THE DISCLOSURE

The present disclosure relates to an atomizer for aerosol delivery devices configured to produce aerosol and which aerosol delivery devices, in some embodiments, may be referred to as electronic cigarettes. In one aspect, an aerosol delivery device is provided that includes a reservoir containing a liquid aerosol precursor composition and an atomizer comprising an electrical resistance heating element and a nonfibrous liquid transport element (which is optionally plate-shaped) having a microtextured surface adapted for surface wicking of the liquid aerosol precursor composition across the microtextured surface, the microtextured surface of the liquid transport element being in fluid communication with the reservoir and in fluid communication with the electric resistance heating element. Use of a microtextured solid surface enables surface wicking of the aerosol precursor composition from a first portion of the liquid transport element into a heating zone proximal to the heating element.

In certain embodiments, the electrical resistance heating element is a film (e.g., a conductive ink) patterned on the microtextured surface of the nonfibrous liquid transport element. The film patterned on the microtextured surface can include one or more straight or curvilinear elements extending from a first end to a second end. A protective layer overlying the electrical resistance heating element can also be included such that liquid aerosol precursor composition transported across the microtextured surface does not directly contact the electrical resistance heating element.

In certain embodiments, the film patterned on the microtextured surface extends from a first end to a second end, and the device further comprises an aperture in the nonfibrous liquid transport element proximal to each of the first end and the second end, and further comprises a positive electric terminal engaged with a first end of the film through an aperture and a negative electric terminal engaged with a second end of the film through an aperture such that an electric current can be passed from terminal to terminal.

In certain embodiments, the device also includes a secondary liquid transport element (e.g., a fibrous material or ceramic material) interposed in a flow path between the reservoir and the nonfibrous liquid transport element and wherein the secondary liquid transport element is in fluid communication with the reservoir and in fluid communication with at least a portion of the nonfibrous liquid transport element. In such embodiments, it is possible for the microtextured surface of the nonfibrous liquid transport element to comprise a heating zone that includes the electrical resistance heating element and a second zone in spaced relation from the electrical resistance heating element, and wherein the secondary liquid transport element is in fluid communication with at least a portion of the second zone such that a flow path for the liquid aerosol precursor composition is established from the secondary liquid transport element to the second zone and from the second zone to the heating zone across the microtextured surface. For example, if the nonfibrous liquid transport element is plate-shaped with a peripheral edge surrounding a central region, the second zone is typically located proximal to the peripheral edge and the heating zone comprises at least a portion of the central region. Alternatively, the secondary liquid transport element can be in fluid communication with all or portions of both the second zone and the heating zone.

The secondary liquid transport element can, for example, overlie at least a portion of the microtextured surface. In certain embodiments, the secondary liquid transport element can overlie substantially all of the microtextured surface. In addition, the device can include at least one aperture through the nonfibrous liquid transport element, wherein at least a portion of the secondary liquid transport element passes through the at least one aperture.

The reservoir and atomizer can be, for example, housed in a cartridge adapted for attachment to a control body, the control body comprising an electrical power source configured to provide electrical current flow to the electrical resistance heating element. In addition, the aerosol delivery device can further include one or more of (a) an electrical power source configured to provide electrical current flow to the electrical resistance heating element; (b) a controller adapted for controlling electrical current flow from the electrical power source; and (c) a flow sensor in communication with the controller and adapted to sense a pressure drop within the aerosol delivery device or a portion thereof.

In one particular embodiment, the invention provides an aerosol delivery device, the device comprising: a reservoir containing a liquid aerosol precursor composition; an atomizer comprising a nonfibrous liquid transport element having a microtextured surface adapted for surface wicking of the liquid aerosol precursor composition across the microtextured surface and an electrical resistance heating element in the form of a film patterned on the microtextured surface of the nonfibrous liquid transport element, the film having a first end and a second end, the microtextured surface of the liquid transport element being in fluid communication with the reservoir and in fluid communication with the electrical resistance heating element; and an aperture in the nonfibrous liquid transport element proximal to each of the first end and the second end, and further comprising a positive electric terminal engaged with a first end of the film through an aperture and a negative electric terminal engaged with a second end of the film through an aperture such that an electric current can be passed from terminal to terminal.

The above-noted device can further include a secondary liquid transport element interposed in a flow path between the reservoir and the nonfibrous liquid transport element and wherein the secondary liquid transport element is in fluid communication with the reservoir and in fluid communication with at least a portion of the nonfibrous liquid transport element. Still further, the microtextured surface of the nonfibrous liquid transport element can comprise a heating zone that includes the electrical resistance heating element and a second zone in spaced relation from the electrical resistance heating element as described above. In addition, the nonfibrous liquid transport element can be plate-shaped with a peripheral edge surrounding a central region, and wherein the second zone is typically located proximal to the peripheral edge and the heating zone comprises at least a portion of the central region.

These and other features, aspects, and advantages of the disclosure will be apparent from a reading of the following detailed description together with the accompanying drawings, which are briefly described below.

BRIEF DESCRIPTION OF THE FIGURES

Having thus described the disclosure in the foregoing general terms, reference will now be made to the accompanying drawings, which are not necessarily drawn to scale, and wherein:

FIG. 1 illustrates an aerosol delivery device comprising a cartridge and a control body in an assembled configuration according to an example embodiment of the present disclosure;

FIG. 2 illustrates the control body of FIG. 1 in an exploded configuration according to an example embodiment of the present disclosure;

FIG. 3 illustrates the cartridge of FIG. 1 in an exploded configuration according to an example embodiment of the present disclosure;

FIG. 4 illustrates a top view of an atomizer according to an example embodiment of the present disclosure;

FIG. 5 illustrates a top view of an atomizer according to a further example embodiment of the present disclosure;

FIG. 6 illustrates a top view of an atomizer according to yet another example embodiment of the present disclosure;

FIG. 7 illustrates a side view of an atomizer with a protective layer according to an example embodiment of the present disclosure;

FIGS. 8A and 8B illustrate a perspective view and an exploded configuration, respectively, of a cartridge according to a further example embodiment of the present disclosure;

FIG. 9 illustrates a perspective view of a cartridge according to yet another example embodiment of the present disclosure;

FIG. 10 illustrates a cross-sectional view of the cartridge of FIG. 9; and FIG. 11 illustrates a further cross-sectional view of the atomizer portion of the cartridge of FIG. 9 with the liquid transport element with the microtextured surface shown at full size.

DETAILED DESCRIPTION OF PREFERRED EMBODIMENTS

The present disclosure will now be described more fully hereinafter with reference to exemplary embodiments thereof. These exemplary embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in the specification, and in the appended claims, the singular forms “a”, “an”, “the”, include plural variations unless the context clearly dictates otherwise.

The invention provides an aerosol delivery device that includes a reservoir containing a liquid aerosol precursor composition and an atomizer. The atomizer includes an electric resistance heating element and a nonfibrous liquid transport element having a microtextured surface adapted for surface wicking of the liquid aerosol precursor composition across the microtextured surface. The microtextured surface is in fluid communication with the reservoir and in fluid communication with the electric resistance heating element, meaning the microtextured surface provides at least a portion of the flow path for the liquid aerosol precursor composition between the reservoir and the heating element. As noted, the liquid transport element is preferably nonfibrous, meaning the liquid transport element is formed from a solid material having a microtextured surface rather than a surface formed by a plurality of bundled fibers.

As notes herein, “microtextured” refers to a surface having topographical three-dimensional features at the micro-meter scale (e.g., a plurality of three-dimensional surface features having an average height of less than about 250 microns) that are discontinuous in appearance such that the surface includes multiple concave and convex portions. Such a surface can also be referred to as roughened or micro-patterned, although the surface features of the microtextured surface can be either an ordered array of structures that follow a pattern or relatively random in arrangement. In certain embodiments, the microtextured surface can be quantified using root mean square (RMS) analysis, with exemplary ranges including Sq values of from about 3 to about 16 microns (e.g., about 4 to about 15 microns including about 4 microns, about 5 microns, about 6 microns, about 7 microns, about 8 microns, about 9 microns, about 10 microns, about 11 microns, about 12 microns, about 13 microns, about 14 microns, and about 15 microns). Certain embodiments have an Sq range of about 3 microns to about 6 microns, about 6 microns to about 10 microns, or about 12 microns to about 15 microns. RMS data can be generated using a Zeiss LSM 800 instrument (confocal microscope) and following the ISO 25178 protocol.

The microtextured surface can exhibit a variety of geometries (e.g., pillars, channels, platelets, cones, divots, etc.). In addition, the microtextured surface can be substantially constant (e.g., exhibiting a single, repeating feature of substantially unchanging dimensions) and/or can exhibit a substantially repeating pattern (e.g., a plurality of features differing in one or more of size, shape, and spacing, that define an ordered, repeating pattern). However, without departing from the invention, the microtextured surface could also exhibit a relatively non-uniform or irregular plurality of surface protrusions. The microtextured surface can be defined at least in part in relation to the size and/or spacing of the geometric elements forming the microtexture. For example, the geometric elements can have an average height of about 1 μm to about 250 μm, about 1.5 μm to about 200 μm, about 2 μm to about 100 μm, about 2.5 μm to about 50 μm, or about 3 μm to about 25 μm. The geometric elements can have an average spacing of about 0.1 μm to about 20 μm, about 0.25 μm to about 15 μm, about 0.5 μm to about 10 μm, or about 1 μm to about 5 μm.

The microtextured surface is adapted to provide surface wicking, sometimes referred to as "hemi-wicking," across the surface such that a steady supply of liquid aerosol precursor composition is delivered directly into close proximity of the heating element. In certain embodiments, this wicking phenomenon can contribute to improved uniformity of heating or vaporization and improved heating efficiency as compared to traditional wick/coil atomizer configurations.

Various embodiments of methods may be employed to form the microtextured surface of the present disclosure. In one example method, the liquid transport element is formed in a mold configured to define the surface including the microtexture. The mold may be etched (e.g., chemical, electrochemical, or laser etched) to define a microtextured surface that is then transferred to the liquid transport element. However, various other embodiments of methods for forming the surface may be employed. For example, the microtextured surface can be produced by one or more methods such as self-assembly of a monolayer, photolithography, machining, lapping (e.g., diamond lapping), plasma spraying, electrospinning, irradiation, template methods, chemical deposition, wet etching, dry etching, and blasting (e.g., with sand, sodium bicarbonate, or dry ice, optionally followed by anodizing the blasted surface). Various examples of such methods for producing surfaces including a micro-pattern are described in *Artificial Lotus Leaf Structures Made by Blasting with Sodium Bicarbonate* by Lee et al., which is incorporated herein by reference in its entirety.

The electric resistance heating element can comprise a metal or like material as otherwise described herein suitable for providing resistive heating. Although the heating element can be placed on a separate substrate or otherwise spaced apart from the microtextured surface (although still in fluid communication therewith), it is advantageous for the heating element to be physically combined with the liquid transport element having the microtextured surface, such as by various means that include etching techniques, printing techniques, or adhering techniques. For example, a metal ribbon can be laminated or otherwise affixed to the liquid transport element.

Advantageously, the electric resistance heating element is in the form of a film patterned on the microtextured surface of the liquid transport element. The thickness of the electrically conductive film layer can vary and can be, for example, about 1,000 μm or less, about 500 μm or less, about 200 μm or less, about 100 μm or less, about 50 μm or less, about 10 μm or less, or about 5 μm or less. In other embodiments, the electrically conductive film layer can have a thickness of about 0.1 μm to about 500 about 0.5 μm to about 200 about 1 μm to about 100 or about 2 μm to about 50 μm.

Where a conductive film is used, the electrically conductive material used in the heating element can comprise essentially any material that is both electrically conductive and suitable for thin film formation. For example, the electrically conductive material can be selected from the group consisting of elemental metals, metal alloys, silicon (including single crystal silicon and poly-silicon), ceramics, carbon, carbides, nitrides, and combinations thereof. In more specific embodiments, the electrically conductive material can be formed of platinum, gold, silver, copper, aluminum, tungsten, zinc, palladium, nickel, titanium, nichrome, silicon carbide, poly-silicon, single crystal silicon, titanium nitride, and the like. In particular embodiments, elemental metals, such as platinum, can be particularly beneficial due to exhibiting good oxidation resistance and long-term stability.

In certain embodiments, an electrically conductive ink can be printed on the surface of the heating element as a patterned film. A heating element formed from an electrically conductive ink can be configured in a variety of patterns of varying complexity. Exemplary conductive inks include graphene inks and inks containing various metals, such as inks including silver, gold, palladium, platinum, and alloys or other combinations thereof (e.g., silver-palladium or silver-platinum inks).

In aspects implementing the imprinting of a conductive ink (e.g., a silver-containing ink), the ink may be applied using a variety of printing processes such as, for instance, gravure printing, flexographic printing, off-set printing, screen printing, ink-jet printing, or other appropriate printing method, in order to provide varying thicknesses, patterns, surface coverage, and composition gradients. Printing of an electrically conductive ink on the fluid transport element can improve manufacturing in that fewer materials and/or fewer processing steps may be required, and high throughput printing techniques can be utilized to rapidly prepare the heating element. In addition, it has been discovered that printing a thin film heating element on the microtextured surface can enhance durability of the heating element by reducing film cracking and other discontinuations that can result either during drying of the ink or when applying a current to the ink. Still further, in certain embodiments, the use of a microtextured surface in combination with a thin film heating element applied thereto is believed to provide reduced charring/pyrolysis as compared to traditional wick/coil atomizer arrangements.

The liquid transport element with the microtextured surface can be formed of a substrate material that is preferably thermally and mechanically stable under the conditions of use. For example, the liquid transport element may be formed of a material that is temperature stable at a temperature of about 100° C. or greater, about 150° C. or greater, about 200° C. or greater, about 300° C. or greater, about 400° C. or greater, or about 500° C. or greater. In other embodiments, the liquid transport element can be temperature stable in a temperature range of about 100° C. to about 750° C., about 125° C. to about to about 650° C., or about 150° C. to about 500° C. In some embodiments, the liquid transport element can be formed of a ceramic material, particularly a silicon-based material, such as a silicon nitride or silicon dioxide material. Other materials, however, such as glass or quartz can be used. Certain thermoplastic materials, such as cyclic olefin copolymers (COC), also can be used.

In some embodiments, the liquid transport element can have a relatively small thickness—e.g., about 1 mm to about 20 mm, about 1.5 mm to about 15 mm, or about 2 mm to about 10 mm. In some embodiments, the liquid transport element can have a surface area of about 0.5 $cm^2$ to about 50 $cm^2$, about 1 $cm^2$ to about 45 $cm^2$, about 2 $cm^2$ to about 40 $cm^2$, or about 3 $cm^2$ to about 30 $cm^2$. The liquid transport element can be characterized in relation to its further dimensions as well. Specifically, the liquid transport element can have a length and a width that are independently up to about 25 mm, up to about 20 mm, up to about 15 mm, or up to about 10 mm. In other embodiments, the length and width of the liquid transport element independently can be about 0.25 mm to about 25 mm, about 0.5 mm to about 15 mm, about 0.6 mm to about 10 mm, about 0.7 mm to about 7.5 mm, or about 0.75 mm to about 5 mm.

In certain embodiments, the liquid transport element can be plate-shaped, meaning a shape that is substantially flat and has a length and a width that are both greater than the thickness. Such a liquid transport element may be substantially square or rectangular; however, other shapes (e.g., round, oval, triangular, or other multi-sided shapes) could also be used. Additional geometries for the liquid transport element could also be used, such as cylindrical shapes.

The present disclosure provides descriptions of aerosol delivery devices. The aerosol delivery devices may use electrical energy to heat a material (preferably without combusting the material to any significant degree) to form an inhalable substance; such articles most preferably being sufficiently compact to be considered "hand-held" devices. An aerosol delivery device may provide some or all of the sensations (e.g., inhalation and exhalation rituals, types of tastes or flavors, organoleptic effects, physical feel, use rituals, visual cues such as those provided by visible aerosol, and the like) of smoking a cigarette, cigar, or pipe, without any substantial degree of combustion of any component of that article or device. The aerosol delivery device may not produce smoke in the sense of the aerosol resulting from by-products of combustion or pyrolysis of tobacco, but rather, that the article or device most preferably yields vapors (including vapors within aerosols that can be considered to be visible aerosols that might be considered to be described as smoke-like) resulting from volatilization or vaporization of certain components of the article or device, although in other embodiments the aerosol may not be visible. In highly preferred embodiments, aerosol delivery devices may incorporate tobacco and/or components derived from tobacco. As such, the aerosol delivery device can be characterized in certain embodiments as an electronic smoking article such as an electronic cigarette or "e-cigarette."

While the systems are generally described herein in terms of embodiments associated with aerosol delivery devices such as so-called "e-cigarettes," it should be understood that the mechanisms, components, features, and methods may be embodied in many different forms and associated with a variety of articles. For example, the description provided herein may be employed in conjunction with embodiments of traditional smoking articles (e.g., cigarettes, cigars, pipes, etc.) or heat-not-burn smoking articles. Accordingly, it should be understood that the description of the mechanisms, components, features, and methods disclosed herein are discussed in terms of embodiments relating to aerosol delivery devices by way of example only, and may be embodied and used in various other products and methods.

Aerosol delivery devices of the present disclosure also can be characterized as being vapor-producing articles or medicament delivery articles. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "aerosol" as used herein is meant to include vapors, gases and aerosols of a form or type suitable for human inhalation, whether or not visible, and whether or not of a form that might be considered to be smoke-like.

In use, aerosol delivery devices of the present disclosure may be subjected to many of the physical actions employed by an individual in using a traditional type of smoking article (e.g., a cigarette, cigar or pipe that is employed by lighting and inhaling tobacco). For example, the user of an aerosol delivery device of the present disclosure can hold that article much like a traditional type of smoking article, draw on one end of that article for inhalation of aerosol produced by that article, take puffs at selected intervals of time, etc.

The invention will now be described by reference to various figures. Aerosol delivery devices of the present disclosure generally include a number of components provided within an outer shell or body. The overall design of the outer shell or body can vary, and the format or configuration of the outer body that can define the overall size and shape of the aerosol delivery device can vary. Typically, an elongated body resembling the shape of a cigarette or cigar can be a formed from a single, unitary shell; or the elongated body can be formed of two or more separable pieces. For example, an aerosol delivery device can comprise an elongated shell or body that can be substantially tubular in shape and, as such, resemble the shape of a conventional cigarette or cigar. However, various other shapes and configurations may be employed in other embodiments (e.g., rectangular or fob-shaped).

In one embodiment, all of the components of the aerosol delivery device are contained within one outer body or shell. Alternatively, an aerosol delivery device can comprise two or more shells that are joined and are separable. For example, an aerosol delivery device can possess at one end a control body comprising a shell containing one or more reusable components (e.g., a rechargeable battery and various electronics for controlling the operation of that article), and at the other end and removably attached thereto a shell containing a disposable portion (e.g., a disposable flavor-containing cartridge). More specific formats, configurations and arrangements of components within the single shell type of unit or within a multi-piece separable shell type of unit will be evident in light of the further disclosure provided herein. Additionally, various aerosol delivery device designs and component arrangements can be appreciated upon consideration of the commercially available electronic aerosol delivery devices.

Aerosol delivery devices of the present disclosure most preferably comprise some combination of a power source (i.e., an electrical power source), at least one control component (e.g., means for actuating, controlling, regulating and/or ceasing power for heat generation, such as by controlling electrical current flow from the power source to other components of the aerosol delivery device), a heater or heat generation component (e.g., an electrical resistance heating element or component commonly referred to as part of an "atomizer"), and an aerosol precursor composition (e.g., commonly a liquid capable of yielding an aerosol upon application of sufficient heat, such as ingredients commonly referred to as "smoke juice," "e-liquid" and "e-juice"), and a mouthend region or tip for allowing draw upon the aerosol delivery device for aerosol inhalation (e.g., a defined air flow path through the article such that aerosol generated can be withdrawn therefrom upon draw).

Alignment of the components within the aerosol delivery device of the present disclosure can vary. In specific embodiments, the aerosol precursor composition can be located near an end of the aerosol delivery device which may be configured to be positioned proximal to the mouth of a user so as to maximize aerosol delivery to the user. Other configurations, however, are not excluded. Generally, the heating element can be positioned sufficiently near the aerosol precursor composition so that heat from the heating element can volatilize the aerosol precursor (as well as one or more flavorants, medicaments, or the like that may likewise be provided for delivery to a user) and form an aerosol for delivery to the user. When the heating element heats the aerosol precursor composition, an aerosol is formed, released, or generated in a physical form suitable for inhalation by a consumer. It should be noted that the foregoing terms are meant to be interchangeable such that reference to release, releasing, releases, or released includes form or generate, forming or generating, forms or generates, and formed or generated. Specifically, an inhalable substance is released in the form of a vapor or aerosol or mixture thereof, wherein such terms are also interchangeably used herein except where otherwise specified.

As noted above, the aerosol delivery device may incorporate a battery or other electrical power source (e.g., a capacitor) to provide current flow sufficient to provide various functionalities to the aerosol delivery device, such as powering of a heater, powering of control systems, powering of indicators, and the like. The power source can take on various embodiments. Preferably, the power source is able to deliver sufficient power to rapidly heat the heating element to provide for aerosol formation and power the aerosol delivery device through use for a desired duration of time. The power source preferably is sized to fit conveniently within the aerosol delivery device so that the aerosol delivery device can be easily handled. Additionally, a preferred power source is of a sufficiently light weight to not detract from a desirable smoking experience.

More specific formats, configurations and arrangements of components within the aerosol delivery device of the present disclosure will be evident in light of the further disclosure provided hereinafter. Additionally, the selection of various aerosol delivery device components can be appreciated upon consideration of the commercially available electronic aerosol delivery devices. Further, the arrangement of the components within the aerosol delivery device can also be appreciated upon consideration of the commercially available electronic aerosol delivery devices. Examples of commercially available products, for which the components thereof, methods of operation thereof, materials included therein, and/or other attributes thereof may be included in the devices of the present disclosure have been marketed as ACCORD® by Philip Morris Incorporated; ALPHA™, JOYE 510™ and M4™ by InnoVapor LLC; CIRRUS™ and FLING™ by White Cloud Cigarettes; BLU™ by Lorillard Technologies, Inc.; COHITA™, COLIBRI™, ELITE CLASSIC™, MAGNUM™, PHANTOM™ and SENSE™ by Epuffer® International Inc.; DUOPRO™, STORM™ and VAPORKING® by Electronic Cigarettes, Inc.; EGAR™ by Egar Australia; eGo-C™ and eGo-T™ by Joyetech; ELUSION™ by Elusion UK Ltd; EONSMOKE® by Eonsmoke LLC; FIN' by FIN Branding Group, LLC; SMOKE® by Green Smoke Inc. USA; GREENARETTE™ by Greenarette LLC; HALLIGAN™ HENDU™ JET™, MAXXQ™ PINK™ and PITBULL™ by Smoke Stik®; HEATBAR™ by Philip Morris International, Inc.; HYDRO IMPERIAL™ and LXE™ from Crown7; LOGIC™ and THE CUBAN™ by LOGIC Technology; LUCI® by Luciano Smokes Inc.; METRO® by Nicotek, LLC; NJOY® and ONEJOY™ by Sottera, Inc.; NO. 7™ by SS Choice LLC; PREMIUM ELECTRONIC CIGARETTE™ by PremiumEstore LLC; RAPP E-MYSTICK™ by Ruyan America, Inc.; RED DRAGON™ by Red Dragon Products, LLC; RUYAN® by Ruyan Group (Holdings) Ltd.; SF® by Smoker Friendly International, LLC; GREEN SMART SMOKER® by The Smart Smoking Electronic Cigarette Company Ltd.; SMOKE ASSIST® by Coastline Products LLC; SMOKING EVERYWHERE® by Smoking Everywhere, Inc.; V2CIGS™ by VMR Products LLC; VAPOR NINE™ by VaporNine LLC; VAPOR4LIFE® by Vapor 4 Life, Inc.; VEPPO™ by E-CigaretteDirect, LLC; AVIGO, VUSE, VUSE CONNECT, VUSE FOB, VUSE HYBRID, ALTO, ALTO+, MODO, CIRO, FOX+FOG, AND SOLO+ by R. J. Reynolds Vapor Company; MISTIC MENTHOL by Mistic Ecigs; and VYPE by CN Creative Ltd. Yet other electrically powered aerosol delivery devices, and in particular those devices that have been characterized as so-called electronic cigarettes, have been marketed under the tradenames COOLER VISIONS™; DIRECT E-CIG™; DRAGONFLY™; EMIST™; EVERSMOKE™; GAMUCCI®; HYBRID FLAME™; KNIGHT STICKS™; ROYAL BLUES™; SMOKETIP®; SOUTH BEACH SMOKE™.

Additional manufacturers, designers, and/or assignees of components and related technologies that may be employed in the aerosol delivery device of the present disclosure include Shenzhen Jieshibo Technology of Shenzhen, China; Shenzhen First Union Technology of Shenzhen City, China; Safe Cig of Los Angeles, Calif.; Janty Asia Company of the Philippines; Joyetech Changzhou Electronics of Shenzhen, China; SIS Resources; B2B International Holdings of Dover, Del.; Evolv LLC of OH; Montrade of Bologna, Italy; Shenzhen Bauway Technology of Shenzhen, China; Global Vapor Trademarks Inc. of Pompano Beach, Fla.; Vapor Corp. of Fort Lauderdale, Fla.; Nemtra GMBH of Raschau-Markersbach, Germany; Perrigo L. Co. of Allegan, Mich.; Needs Co., Ltd.; Smokefree Innotec of Las Vegas, Nev.;

McNeil AB of Helsingborg, Sweden; Chong Corp; Alexza Pharmaceuticals of Mountain View, Calif.; BLEC, LLC of Charlotte, N.C.; Gaitrend Sarl of Rohrbach-les-Bitche, France; FeelLife Bioscience International of Shenzhen, China; Vishay Electronic BMGH of Selb, Germany; Shenzhen Smaco Technology Ltd. of Shenzhen, China; Vapor Systems International of Boca Raton, Fla.; Exonoid Medical Devices of Israel; Shenzhen Nowotech Electronic of Shenzhen, China; Minilogic Device Corporation of Hong Kong, China; Shenzhen Kontle Electronics of Shenzhen, China, and Fuma International, LLC of Medina, Ohio, 21st Century Smoke of Beloit, Wis., and Kimree Holdings (HK) Co. Limited of Hong Kong, China.

One example embodiment of an aerosol delivery device 100 is illustrated in FIG. 1. In particular, FIG. 1 illustrates an aerosol delivery device 100 including a control body 200 and a cartridge 300. The control body 200 and the cartridge 300 can be permanently or detachably aligned in a functioning relationship. Various mechanisms may connect the cartridge 300 to the control body 200 to result in a threaded engagement, a press-fit engagement, an interference fit, a magnetic engagement, or the like. The aerosol delivery device 100 may be substantially rod-like, substantially tubular shaped, or substantially cylindrically shaped in some embodiments when the cartridge 300 and the control body 200 are in an assembled configuration. However, as noted above, various other configurations such as rectangular or fob-shaped may be employed in other embodiments. Further, although the aerosol delivery devices are generally described herein as resembling the size and shape of a traditional smoking article, in other embodiments differing configurations and larger capacity reservoirs, which may be referred to as "tanks," may be employed.

In specific embodiments, one or both of the cartridge 300 and the control body 200 may be referred to as being disposable or as being reusable. For example, the control body 200 may have a replaceable battery or a rechargeable battery and/or capacitor and thus may be combined with any type of recharging technology, including connection to a typical alternating current electrical outlet, connection to a car charger (i.e., cigarette lighter receptacle), and connection to a computer, such as through a universal serial bus (USB) cable. Further, in some embodiments the cartridge 300 may comprise a single-use cartridge, as disclosed in U.S. Pat. No. 8,910,639 to Chang et al., which is incorporated herein by reference in its entirety.

Figure 2:
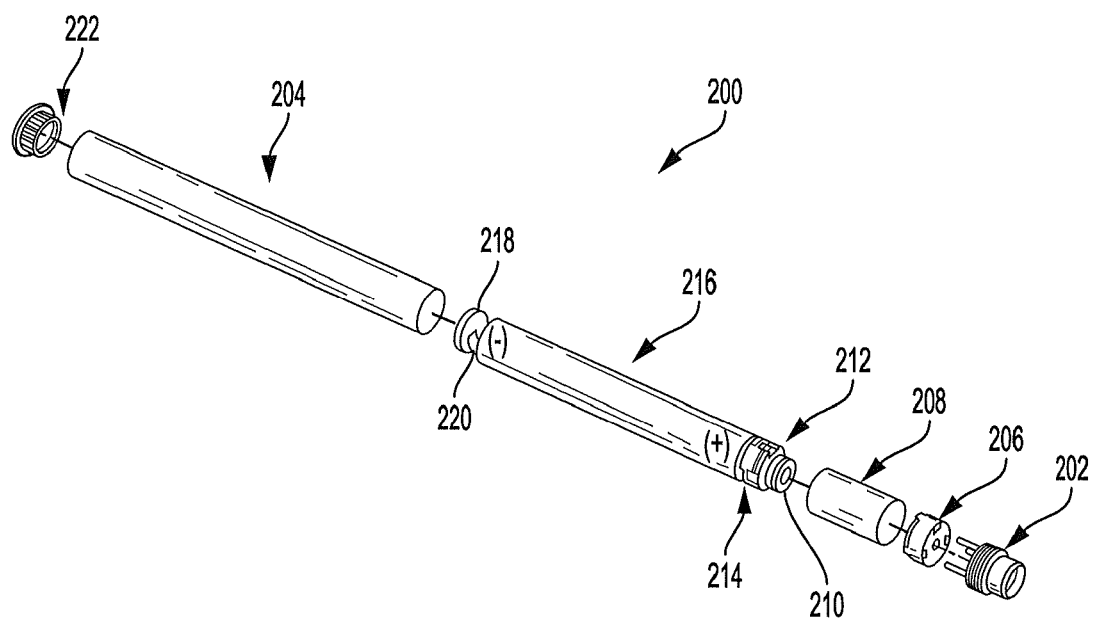

FIG. 2 illustrates an exploded view of the control body 200 of the aerosol delivery device 100 (see, FIG. 1) according to an example embodiment of the present disclosure. As illustrated, the control body 200 may comprise a coupler 202, an outer body 204, a sealing member 206, an adhesive member 208 (e.g., KAPTON® tape), a flow sensor 210 (e.g., a puff sensor or pressure switch), a control component 212, a spacer 214, an electrical power source 216 (e.g., a capacitor and/or a battery, which may be rechargeable), a circuit board with an indicator 218 (e.g., a light emitting diode (LED)), a connector circuit 220, and an end cap 222. Examples of electrical power sources are described in U.S. Pat. App. Pub. No. 2010/0028766 by Peckerar et al., the disclosure of which is incorporated herein by reference in its entirety.

With respect to the flow sensor 210, representative current regulating components and other current controlling components including various microcontrollers, sensors, and switches for aerosol delivery devices are described in U.S. Pat. No. 4,735,217 to Gerth et al., U.S. Pat. Nos. 4,922,901, 4,947,874, and 4,947,875, all to Brooks et al., U.S. Pat. No. 5,372,148 to McCafferty et al., U.S. Pat. No. 6,040,560 to Fleischhauer et al., U.S. Pat. No. 7,040,314 to Nguyen et al., and U.S. Pat. No. 8,205,622 to Pan, all of which are incorporated herein by reference in their entireties. Reference also is made to the control schemes described in U.S. App. Pub. No. 2014/0270727 to Ampolini et al., which is incorporated herein by reference in its entirety.

In one embodiment the indicator 218 may comprise one or more light emitting diodes. The indicator 218 can be in communication with the control component 212 through the connector circuit 220 and be illuminated, for example, during a user drawing on a cartridge coupled to the coupler 202, as detected by the flow sensor 210. The end cap 222 may be adapted to make visible the illumination provided thereunder by the indicator 218. Accordingly, the indicator 218 may be illuminated during use of the aerosol delivery device 100 to simulate the lit end of a smoking article. However, in other embodiments the indicator 218 can be provided in varying numbers and can take on different shapes and can even be an opening in the outer body (such as for release of sound when such indicators are present).

Still further components can be utilized in the aerosol delivery device of the present disclosure. For example, U.S. Pat. No. 5,154,192 to Sprinkel et al. discloses indicators for smoking articles; U.S. Pat. No. 5,261,424 to Sprinkel, Jr. discloses piezoelectric sensors that can be associated with the mouth-end of a device to detect user lip activity associated with taking a draw and then trigger heating of a heating device; U.S. Pat. No. 5,372,148 to McCafferty et al. discloses a puff sensor for controlling energy flow into a heating load array in response to pressure drop through a mouthpiece; U.S. Pat. No. 5,967,148 to Harris et al. discloses receptacles in a smoking device that include an identifier that detects a non-uniformity in infrared transmissivity of an inserted component and a controller that executes a detection routine as the component is inserted into the receptacle; U.S. Pat. No. 6,040,560 to Fleischhauer et al. describes a defined executable power cycle with multiple differential phases; U.S. Pat. No. 5,934,289 to Watkins et al. discloses photonic-optronic components; U.S. Pat. No. 5,954,979 to Counts et al. discloses means for altering draw resistance through a smoking device; U.S. Pat. No. 6,803,545 to Blake et al. discloses specific battery configurations for use in smoking devices; U.S. Pat. No. 7,293,565 to Griffen et al. discloses various charging systems for use with smoking devices; U.S. Pat. No. 8,402,976 to Fernando et al. discloses computer interfacing means for smoking devices to facilitate charging and allow computer control of the device; U.S. Pat. No. 8,689,804 to Fernando et al. discloses identification systems for smoking devices; and WO 2010/003480 by Flick discloses a fluid flow sensing system indicative of a puff in an aerosol generating system; all of the foregoing disclosures being incorporated herein by reference in their entireties. Further examples of components related to electronic aerosol delivery articles and disclosing materials or components that may be used in the present article include U.S. Pat. No. 4,735,217 to Gerth et al.; U.S. Pat. No. 5,249,586 to Morgan et al.; U.S. Pat. No. 5,666,977 to Higgins et al.; U.S. Pat. No. 6,053,176 to Adams et al.; U.S. Pat. No. 6,164,287 to White; U.S. Pat. No. 6,196,218 to Voges; U.S. Pat. No. 6,810,883 to Felter et al.; U.S. Pat. No. 6,854,461 to Nichols; U.S. Pat. No. 7,832,410 to Hon; U.S. Pat. No. 7,513,253 to Kobayashi; U.S. Pat. No. 7,896,006 to Hamano; U.S. Pat. No. 6,772,756 to Shayan; U.S. Pat. Nos. 8,156,944 and 8,375,957 to Hon; U.S. Pat. No. 8,794,231 to Thorens et al.; U.S. Pat. No. 8,851,083 to Oglesby et al.; U.S. Pat. Nos. 8,915,254 and 8,925,555 to Monsees et al.; and U.S. Pat. No. 9,220,302 to DePiano et al.; U.S. Pat. App. Pub. Nos. 2006/0196518 and 2009/0188490 to Hon; U.S. Pat. App. Pub. No. 2010/0024834 to Oglesby et al.; U.S. Pat. App. Pub. No. 2010/0307518 to Wang; WO 2010/091593 to Hon; and WO 2013/089551 to Foo, each of which is incorporated herein by reference in its entirety. A variety of the materials disclosed by the foregoing documents may be incorporated into the present devices in various embodiments, and all of the foregoing disclosures are incorporated herein by reference in their entireties.

Figure 3:
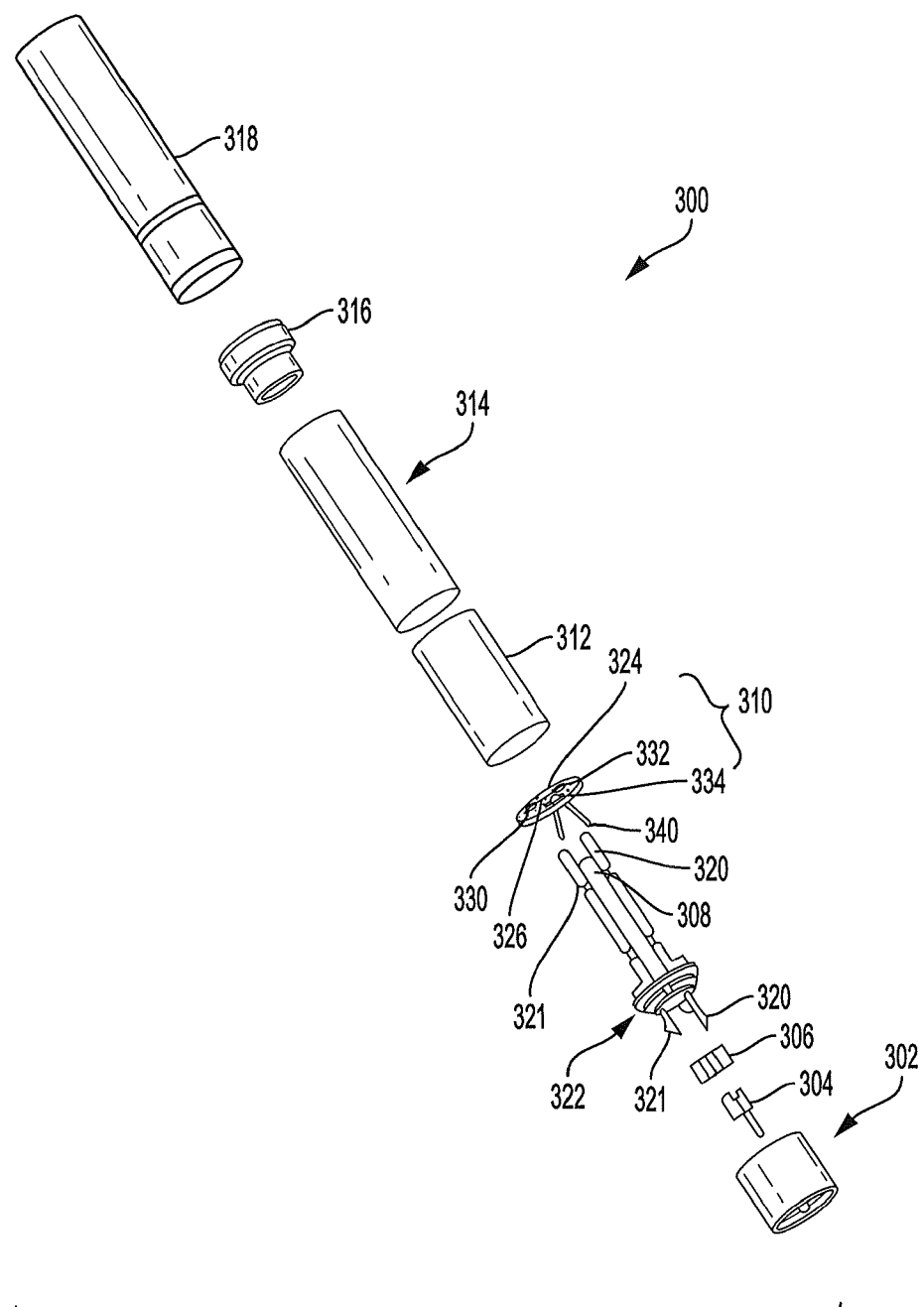

FIG. 3 illustrates the cartridge 300 of the aerosol delivery device 100 (see, FIG. 1) in an exploded configuration. As illustrated, the cartridge 300 may comprise a base 302, a control component terminal 304, an electronic control component 306, a flow director 308, an atomizer 310, a reservoir 312 (e.g., a reservoir substrate), an outer body 314, a mouthpiece 316, a label 318, and first and second heating terminals 320, 321 according to an example embodiment of the present disclosure.

In some embodiments the first and second heating terminals 320, 321 may be embedded in, or otherwise coupled to, the flow director 308. For example, the first and second heating terminals 320, 321 may be insert molded in the flow director 308. Accordingly, the flow director 308 and the first and second heating terminals are collectively referred to herein as a flow director assembly 322. Additional description with respect to the first and second heating terminals 320, 321 and the flow director 308 is provided in U.S. Pat. Pub. No. 2015/0335071 to Brinkley et al., which is incorporated herein by reference in its entirety.

In the embodiment shown in FIG. 3, the atomizer 310 may comprise a liquid transport element 324 with a microtextured surface as described herein and a heating element 326 as described herein (e.g., a conductive ink applied to the microtextured surface of the liquid transport element). The liquid transport element 324 can include two apertures 330, 332 that provide an electrical connection between the heating element 326 and the heating terminals 320, 321. The liquid transport element 324 can include a further aperture 334 through which a secondary liquid transport element 340 can extend. In this manner, liquid can be transported from the reservoir 312 to the secondary liquid transport element 340 and then to the microtextured surface of the liquid transport element 324 for hemi-wicking across the surface into a heating zone in proximity to the heating element 326. Although not shown in this embodiment, the liquid transport element 324 could include further apertures, grooves, or notches in order to enhance airflow past the liquid transport element. In addition, although the liquid transport element 324 is shown as positioned with its planar surface approximately perpendicular to the longitudinal axis of the cartridge 300, other orientations are possible including an orientation wherein the liquid transport element is positioned with its planar surface approximately parallel to the longitudinal axis of the cartridge.

The secondary liquid transport element 340 particularly can be a wick that utilizes capillary action in the transport of liquids. A wick for use according to the invention thus can be any material that provides sufficient wicking action to transport one or more components of the aerosol precursor composition to the aerosolization zone. Non-limiting examples include natural and synthetic fibers, such as cotton, cellulose, polyesters, polyamides, polylactic acids, glass fibers, combinations thereof, and the like. Other exemplary materials that can be used in wicks include metals, ceramics, and carbonized materials (e.g., a foam or monolith formed of a carbonaceous material that has undergone calcining to drive off non-carbon components of the material). Wicks further can be coated with materials that alter the capillary action of the fibers, and the fibers used in forming wicks can have specific cross-sectional shape and can be grooved so as to alter the capillary action of the fibers. For example, temperature adaptive polymers can be used. Such adaptive polymers can be coated on fibers or used in other manners, and these polymers are effective for providing altered liquid transport characteristics based on the surrounding conditions. Temperature adaptive polymers particularly can exhibit low transport at reduced temperatures and can exhibit increased transport at increased temperatures. One example is a material known as Adaptive by HeiQ®. Fibers used in forming wicks can be provided singly, bundled, as a woven fabric (including meshes and braids), or as a nonwoven fabric. Porosity of the wick material also can be controlled to alter the capillary action of the wick, including controlling average pore size and total porosity. Separate wicks also can have different lengths. The term "wick" is also intended to encompass capillary tubes, and any combination of elements providing the desired capillary action can be used.

The cartridge may additionally include a base shipping plug engaged with the base and/or a mouthpiece shipping plug engaged with the mouthpiece in order to protect the base and the mouthpiece and prevent entry of contaminants therein prior to use as disclosed, for example, in U.S. Pat. No. 9,220,302 to DePiano et al., which is incorporated herein by reference in its entirety.

The base 302 may be coupled to a first end of the outer body 314 and the mouthpiece 316 may be coupled to an opposing second end of the outer body to substantially or fully enclose other components of the cartridge 300 therein. For example, the control component terminal 304, the electronic control component 306, the flow director 308, the atomizer 310, and the reservoir 312 may be substantially or entirely retained within the outer body 314. The label 318 may at least partially surround the outer body 314, and optionally the base 302, and include information such as a product identifier thereon. The base 302 may be configured to engage the coupler 202 of the control body 200 (see, e.g., FIG. 2). In some embodiments the base 302 may comprise anti-rotation features that substantially prevent relative rotation between the cartridge and the control body as disclosed in U.S. Pat. App. Pub. No. 2014/0261495 to Novak et al., which is incorporated herein by reference in its entirety.

The reservoir 312 may be configured to hold an aerosol precursor composition. Representative types of aerosol precursor components and formulations are also set forth and characterized in U.S. Pat. No. 7,726,320 to Robinson et al., U.S. Pat. No. 8,881,737 to Collett et al., and U.S. Pat. No. 9,254,002 to Chong et al.; and U.S. Pat. Pub. Nos. 2013/0008457 to Zheng et al.; 2015/0020823 to Lipowicz et al.; and 2015/0020830 to Koller, as well as WO 2014/182736 to Bowen et al, the disclosures of which are incorporated herein by reference. Other aerosol precursors that may be employed include the aerosol precursors that have been incorporated in the VUSE® product by R. J. Reynolds Vapor Company, the BLU product by Lorillard Technologies, the MISTIC MENTHOL product by Mistic Ecigs, and the VYPE product by CN Creative Ltd. Also desirable are the so-called "smoke juices" for electronic cigarettes that have been available from Johnson Creek Enterprises LLC. Embodiments of effervescent materials can be used with the aerosol precursor, and are described, by way of example, in U.S. Pat. App. Pub. No. 2012/0055494 to Hunt et al., which is incorporated herein by reference. Further, the use of effervescent materials is described, for example, in U.S. Pat. No. 4,639,368 to Niazi et al.; U.S. Pat. No. 5,178,878 to Wehling et al.; U.S. Pat. No. 5,223,264 to Wehling et al.; U.S. Pat. No. 6,974,590 to Pather et al.; U.S. Pat. No. 7,381,667 to Bergquist et al.; U.S. Pat. No. 8,424,541 to Crawford et al; and U.S. Pat. No. 8,627,828 to Strickland et al.; as well as US Pat. Pub. Nos. 2010/0018539 to Brinkley et al. and 2010/0170522 to Sun et al.; and PCT WO 97/06786 to Johnson et al., all of which are incorporated by reference herein. Additional description with respect to embodiments of aerosol precursor compositions, including description of tobacco or components derived from tobacco included therein, is provided in U.S. patent application Ser. Nos. 15/216,582 and 15/216,590, each filed Jul. 21, 2016 and each to Davis et al., which are incorporated herein by reference in their entireties. In certain embodiments, the aerosol precursor composition can include components such as polyhydric alcohols (e.g., glycerin, propylene glycol, and mixtures thereof), water, nicotinic compounds (e.g., highly purified tobacco-derived nicotine), acids or bases, flavorants, and mixtures thereof.

The reservoir 312 may comprise a plurality of layers of nonwoven fibers formed into the shape of a tube encircling the interior of the outer body 314 of the cartridge 300. Thus, liquid components, for example, can be sorptively retained by the reservoir 312. The reservoir 312 is in fluid connection with the liquid transport element 324 using the secondary liquid transport element 340 as an intervening conduit. Thus, the liquid transport element 324 may be configured to transport liquid from the reservoir 312 to the heating element 326 via a hemi-wicking liquid transport mechanism.

Additional representative heating elements and materials for use therein are described in U.S. Pat. No. 5,060,671 to Counts et al.; U.S. Pat. No. 5,093,894 to Deevi et al.; U.S. Pat. No. 5,224,498 to Deevi et al.; U.S. Pat. No. 5,228,460 to Sprinkel Jr., et al.; U.S. Pat. No. 5,322,075 to Deevi et al.; U.S. Pat. No. 5,353,813 to Deevi et al.; U.S. Pat. No. 5,468,936 to Deevi et al.; U.S. Pat. No. 5,498,850 to Das; U.S. Pat. No. 5,659,656 to Das; U.S. Pat. No. 5,498,855 to Deevi et al.; U.S. Pat. No. 5,530,225 to Hajaligol; U.S. Pat. No. 5,665,262 to Hajaligol; U.S. Pat. No. 5,573,692 to Das et al.; and U.S. Pat. No. 5,591,368 to Fleischhauer et al., the disclosures of which are incorporated herein by reference in their entireties. Further, chemical heating may be employed in other embodiments. Various additional examples of heaters and materials employed to form heaters are described in U.S. Pat. No. 8,881,737 to Collett et al., which is incorporated herein by reference, as noted above.

A variety of heater components may be used in the present aerosol delivery device. In various embodiments, one or more microheaters or like solid state heaters may be used. Microheaters and atomizers incorporating microheaters suitable for use in the presently disclosed devices are described in U.S. Pat. No. 8,881,737 to Collett et al., which is incorporated herein by reference in its entirety.

The first heating terminal 320 and the second heating terminal 321 (e.g., negative and positive heating terminals) are configured to engage opposing ends of the heating element 326 and to form an electrical connection with the control body 200 (see, e.g., FIG. 2) when the cartridge 300 is connected thereto. Further, when the control body 200 is coupled to the cartridge 300, the electronic control component 306 may form an electrical connection with the control body through the control component terminal 304. The control body 200 may thus employ the electronic control component 212 (see, FIG. 2) to determine whether the cartridge 300 is genuine and/or perform other functions. Further, various examples of electronic control components and functions performed thereby are described in U.S. Pat. App. Pub. No. 2014/0096781 to Sears et al., which is incorporated herein by reference in its entirety.

During use, a user may draw on the mouthpiece 316 of the cartridge 300 of the aerosol delivery device 100 (see, FIG. 1). This may pull air through an opening in the control body 200 (see, e.g., FIG. 2) or in the cartridge 300. For example, in one embodiment an opening may be defined between the coupler 202 and the outer body 204 of the control body 200 (see, e.g., FIG. 2), as described in U.S. Pat. No. 9,220,302 to DePiano et al., which is incorporated herein by reference in its entirety. However, the flow of air may be received through other parts of the aerosol delivery device 100 in other embodiments. As noted above, in some embodiments the cartridge 300 may include the flow director 308. The flow director 308 may be configured to direct the flow of air received from the control body 200 to the heating element 326 of the atomizer 310.

A sensor in the aerosol delivery device 100 (e.g., the flow sensor 210 in the control body 200; see, FIG. 2) may sense the puff. When the puff is sensed, the control body 200 may direct current to the heating element 326 through a circuit including the first heating terminal 320 and the second heating terminal 321. Accordingly, the heating element 326 may vaporize the aerosol precursor composition directed to an aerosolization or heating zone from the reservoir 312 by the liquid transport element 324. Thus, the mouthpiece 326 may allow passage of air and entrained vapor (i.e., the components of the aerosol precursor composition in an inhalable form) from the cartridge 300 to a consumer drawing thereon.

Various other details with respect to the components that may be included in the cartridge 300 are provided, for example, in U.S. Pat. App. Pub. No. 2014/0261495 to DePiano et al., which is incorporated herein by reference in its entirety. Additional components that may be included in the cartridge 300 and details relating thereto are provided, for example, in U.S. Pat. Pub. No. 2015/0335071 to Brinkley et al., filed May 23, 2014, which is incorporated herein by reference in its entirety.

Various components of an aerosol delivery device according to the present disclosure can be chosen from components described in the art and commercially available. Reference is made for example to the reservoir and heater system for controllable delivery of multiple aerosolizable materials in an electronic smoking article disclosed in U.S. Pat. App. Pub. No. 2014/0000638 to Sebastian et al., which is incorporated herein by reference in its entirety.

In another embodiment substantially the entirety of the cartridge may be formed from one or more carbon materials, which may provide advantages in terms of biodegradability and absence of wires. In this regard, the heating element may comprise carbon foam, the reservoir may comprise carbonized fabric, and graphite may be employed to form an electrical connection with the power source and control component. An example embodiment of a carbon-based cartridge is provided in U.S. Pat. App. Pub. No. 2013/0255702 to Griffith et al., which is incorporated herein by reference in its entirety.

Figure 4:
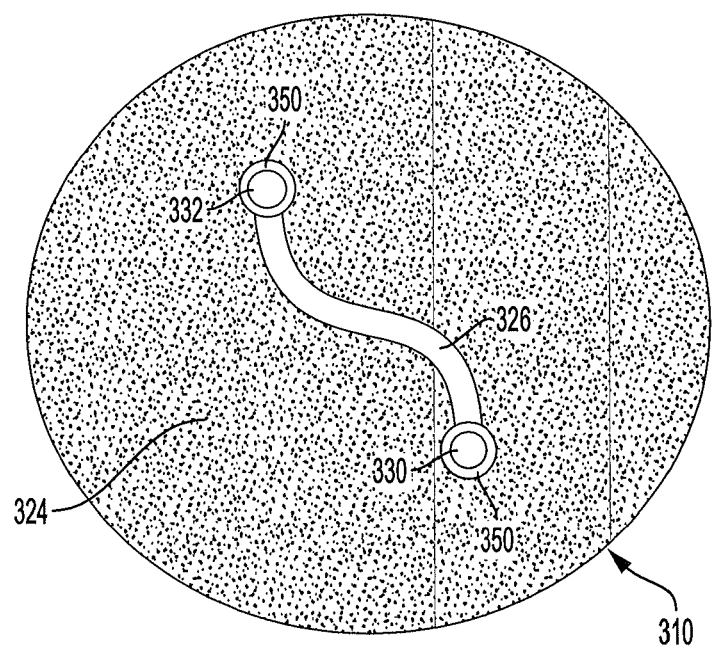

FIG. 4 illustrates a top view of another embodiment of an atomizer 310 that could be used in an aerosol delivery device of the invention. As shown, the atomizer 310 includes a liquid transport element 324 with a microtextured surface upon which a heating element 326 is patterned (e.g., as a conductive ink film).

The heating element 326 extends from a first aperture 330 to a second aperture 332, which serve as points of electrical connection for the heating element. Each aperture provides a space for forming an electrical connection between the heating element 326 and heating terminals (not shown) such as terminals 320, 321 shown in FIG. 3. If desired, a fastener (not shown) formed of a conductive material (e.g., a metal screw) could be inserted in each aperture in order to form part of the electric connection with the heating element 326 and also provide a fastening function for connecting the atomizer 310 to another component of an aerosol delivery device. As shown, each aperture 330, 332 can include an optional conductive coating or film 350 around the periphery of the aperture and extending through at least a portion of the depth of the aperture (and advantageously for the entire depth thereof). The presence of the conductive coating or film, which can be constructed of the same conductive material as the heating element 326, can improve electrical connectivity with the heating element. Note that rather than provide apertures in order to provide electrical connectivity to the heating element 326, electrical connections could be made by connecting the heating element to terminals placed above the microtextured surface, thereby avoiding the need for apertures.

Figure 5:
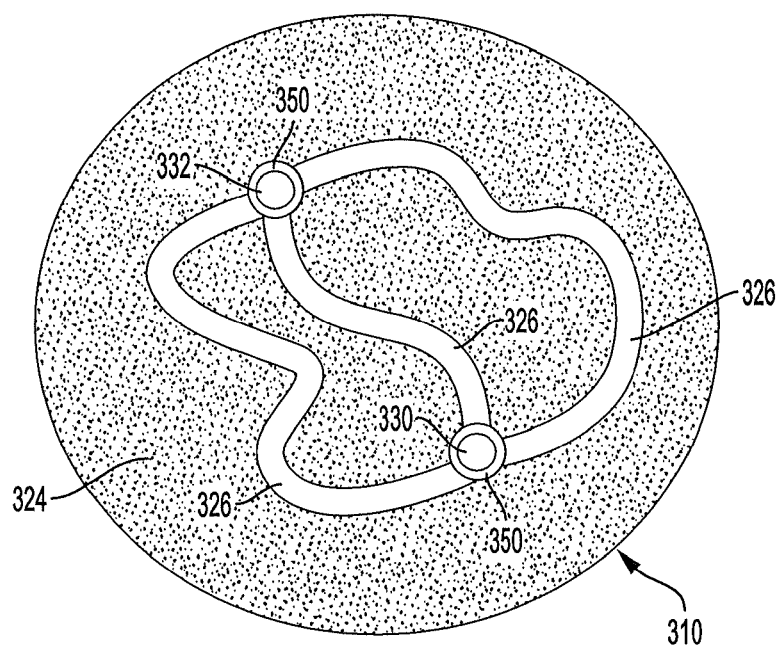

FIG. 5 illustrates a top view of another embodiment of the atomizer 310 similar to FIG. 4 discussed above. However, as illustrated, the heating element 326 is configured in a different pattern such that multiple heating element portions are patterned on the liquid transport element 324 to increase the heating across the surface. The number of heating element portions can vary and will typically include from one to ten heating element portions of varying shape and in varying patterns across the surface, depending on the desired size and shape of the heating zone. Note that the multiple heating element portions can extend from shared apertures as shown or each heating element portion can extend between separate apertures to form completely separate heating elements that can be controlled separately.

Figure 6:
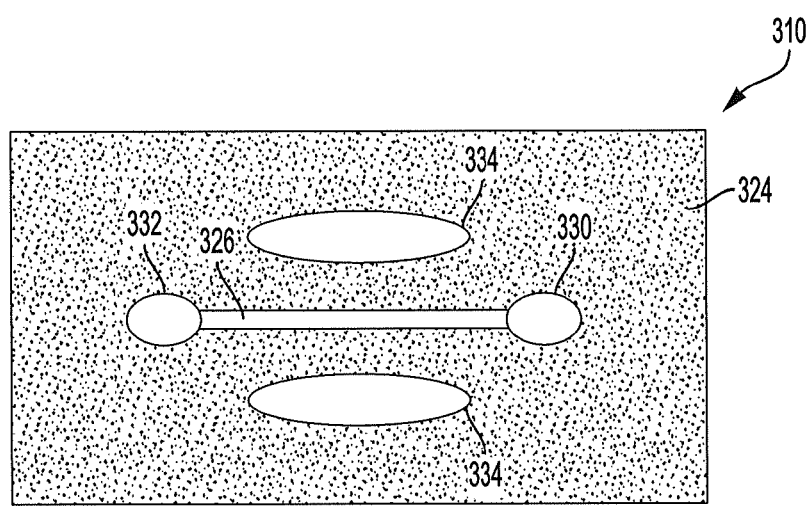

FIG. 6 illustrates the top view of yet another embodiment of an atomizer 310 of the invention. As noted previously, the precise shape of the atomizer 310 can vary, with circular shapes as shown in FIGS. 4 and 5 being one example, and the rectangular shape of FIG. 6 representing another example. Similar to FIG. 4, the atomizer 310 of FIG. 6 includes a heating element 326 (e.g., a conductive ink film) patterned on a liquid transport element 324 having a microtextured surface. The heating element 326 can extend between two apertures 330, 332 that provide a means for electrical connection of the heating element. Similar to FIG. 3, the atomizer 310 of FIG. 6 also includes two apertures 334 through which a secondary fluid transport element (e.g., a fibrous wick), not shown, can pass in order to achieve fluid connection between the microtextured surface and the secondary fluid transport element. In other embodiments, apertures for a secondary fluid transport element could be avoided by positioning the ends of the secondary fluid transport element, which are typically adapted for fluid communication with a reservoir, in a different location, such as overlying the microtextured surface.

The atomizer of the invention can comprise a protective layer overlying the microtextured surface of at least a portion of the liquid transport element. A protective layer can be advantageously used to prevent direct contact between an aerosol precursor composition and the heating element and thereby passivate the heating zone of the atomizer. The protective layer can also serve as a barrier to prevent direct contact between the heating element and any secondary fluid transport element present in the device. The protective layer is typically formed of a material that is temperature stable under the operating temperatures for the atomizer and can be heat radiant and/or heat conductive. For example, the protective layer can be temperature stable at a temperature of about 150° C. or greater, about 200° C. or greater, about 300° C. or greater, about 400° C. or greater, or about 500° C. or greater. In other embodiments, the protective layer can be temperature stable in a temperature range of about 125° C. to about 750° C., about 150° C. to about to about 650° C., or about 175° C. to about 500° C.

The protective layer can be in direct contact with an aerosol precursor composition or component thereof. Accordingly, it is preferable for the protective layer to be substantially chemically non-reactive with the various compounds that may be included in the aerosol precursor material. By substantially chemically non-reactive is meant that any chemical reaction between the protective layer and a component of the aerosol precursor material is sufficiently limited such that the protective layer is not breached so as to allow the aerosol precursor composition to be in direct contact with the electrically conductive layer of the heating element. Alternately, the phrase can mean that any chemical reaction between the protective layer and a component of the aerosol precursor material is sufficiently limited such that chemical compounds present in the protective layer are not released (or new chemical compounds formed) so as to combine with the formed aerosol for inhalation by a consumer.

In certain embodiments, the protective layer can comprise a silicon-based material, such as silicon dioxide, silicon nitride or silicon carbide. Alternatively, the protective layer can be formed of a metal oxide material such as alumina. The thickness of the protective layer can vary, with exemplary thicknesses including about 0.1 micron to about 1.0 micron. Any coating method known in the art could be used to apply the protective layer, including plasma-enhanced chemical vapor deposition (PECVD).

Figure 7:
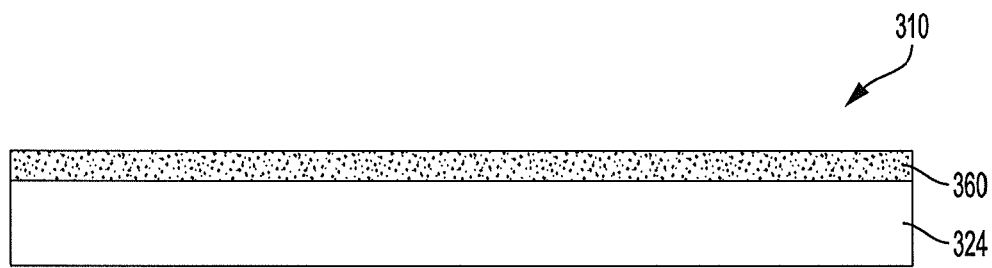

FIG. 7 provides a side view of an atomizer 310 showing a protective layer 360 applied to the microtextured surface of a liquid transport element 324. Note that the protective layer 360 can be applied to all or only a portion of the microtextured surface. For example, the protective layer 360 could be applied to only an area encompassing the heating element (see, FIGS. 4-6) to prevent contact between the heating element and an aerosol precursor composition.

Figure 8A:
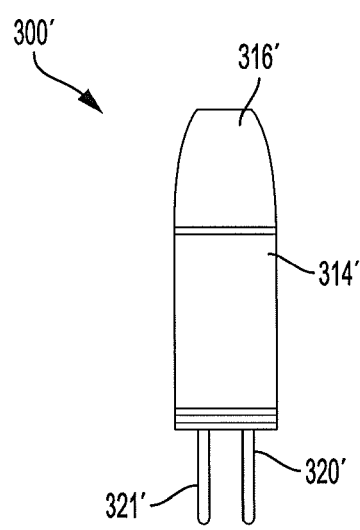
Figure 8B:
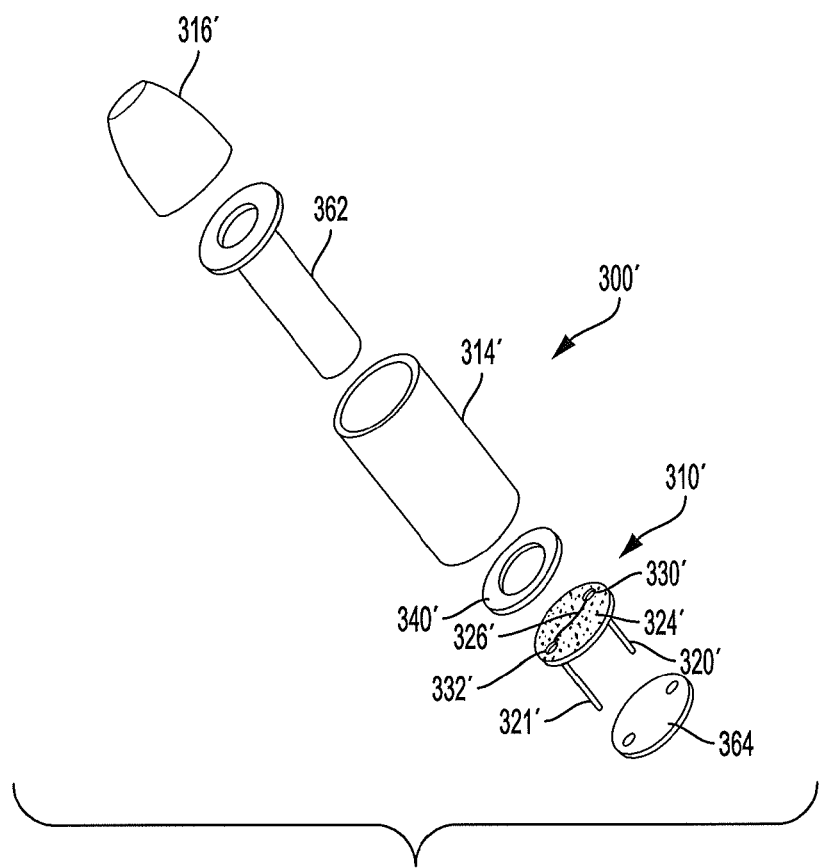

FIG. 8A provides a perspective view of another embodiment of a cartridge 300' that includes a mouthpiece 316', an outer body 314', and heating terminals 320' and 321', which function equivalently as described in connection with FIG. 3. As shown in the exploded view of FIG. 8B, the cartridge 300' can further include a flow tube 362 adapted to channel aerosol from the atomizer 310' to the mouthpiece 316'. An aerosol precursor composition (not shown) can be housed in the reservoir space between the outer body 314' and the outer walls of the tube formed by flow tube 362. The heating terminals 320' and 321' provide an electric connection to the atomizer 310', which includes a liquid transport element 324' with a microtextured surface, a heating element 326' (e.g., a patterned conductive film), and two apertures 330' and 332'. The cartridge 300' further includes a base plate 364. As shown, unlike the embodiment of FIG. 3, the cartridge 300' includes a disc-shaped secondary fluid transport element 340' overlying the periphery of the microtextured surface of the liquid transport element 324'. The secondary fluid transport element 340', which could be constructed of any of the wicking materials noted herein, provides a fluid connection between the reservoir containing aerosol precursor material and the microtextured surface of the liquid transport element 324'.

Figure 9:
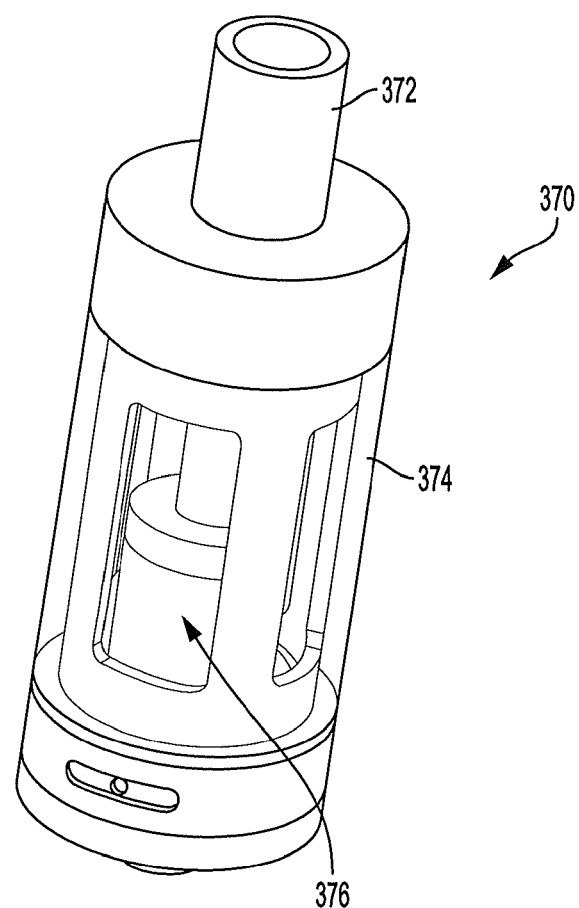
Figure 10:
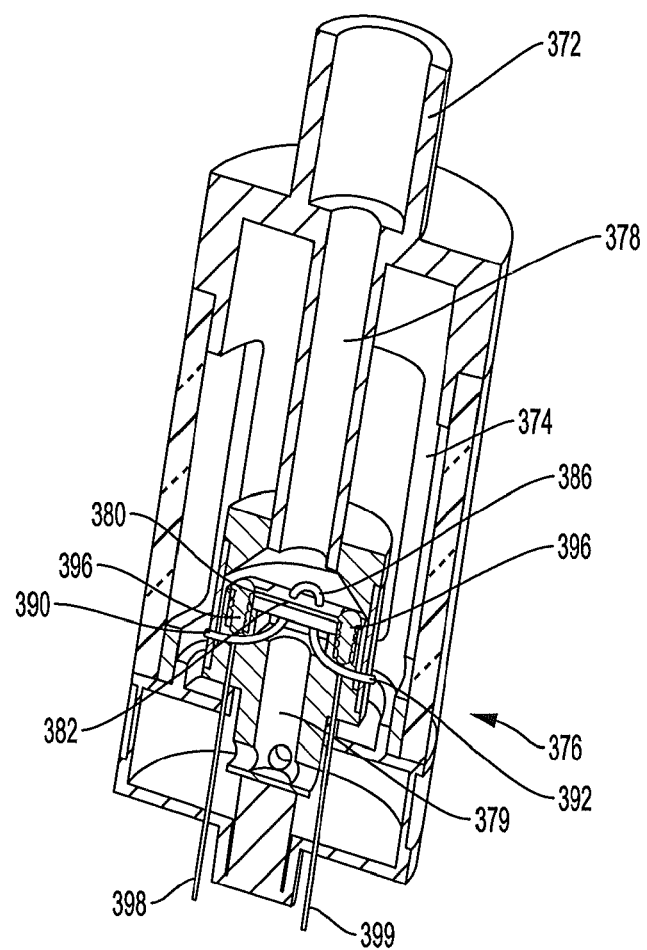
Figure 11:
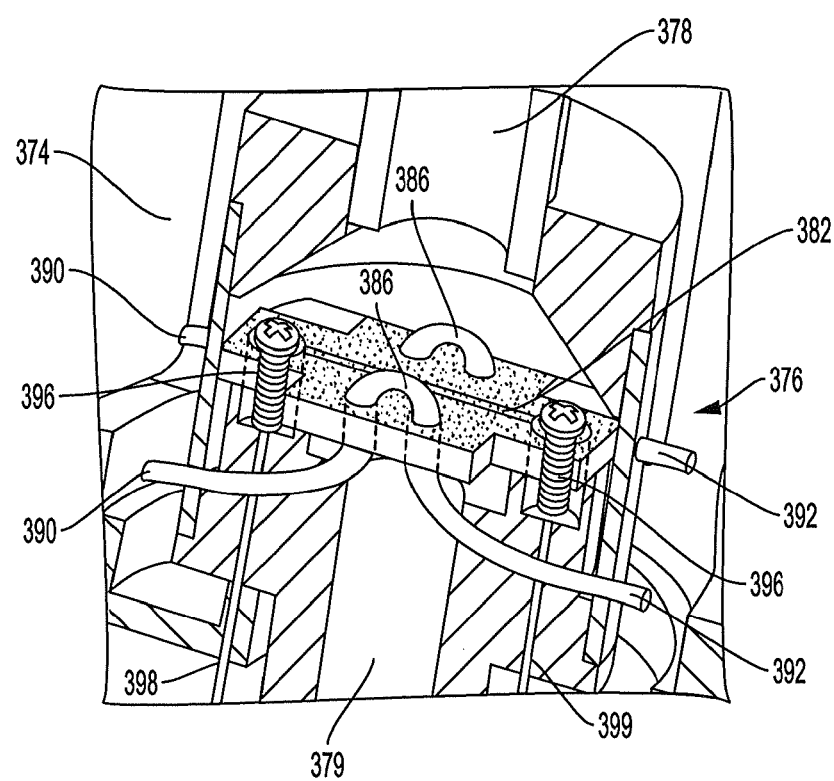

FIGS. 9-11 illustrate a still further embodiment of a cartridge of the present disclosure. As shown in FIG. 9, the cartridge 370 can include a mouthpiece 372 and an outer reservoir 374. An atomizer 376 is located centrally relative to the reservoir 374. As shown in the cross-sectional views of FIGS. 10 and 11, a flow tube 378 provide a path for aerosol to travel from the atomizer 376 to the mouthpiece 372 and a second flow tube 379 that brings air drawn through the device to the atomizer.

Referring to FIGS. 10 and 11, the atomizer 376 includes a liquid transport element 380 with a microtextured surface having an electrically conductive film heating element 382 patterned thereon. The atomizer 376 also includes two longitudinally-extending secondary liquid transport elements 386 (e.g., a fibrous wick or any other wicking material noted herein) that pass through two sets of apertures such that the secondary liquid transport element is in fluid communication with the microtextured surface. The opposing ends 390, 392 of each longitudinally-extending secondary liquid transport element 386 extend into the reservoir 374 and thereby provide a fluid pathway for aerosol precursor composition from the reservoir to the microtextured surface. Screws 396 formed of a conductive material hold the atomizer in 376 in place and form part of the electric connection between the heating element 382 and heating terminals 398, 399.

Many modifications and other embodiments of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

The invention claimed is:

1. An aerosol delivery device, comprising:
  a reservoir containing a liquid aerosol precursor composition;
  an atomizer comprising an electrical resistance heating element in the form of a pattern on a microtextured surface of a nonfibrous liquid transport element adapted for surface wicking of the liquid aerosol precursor composition across the microtextured surface, the microtextured surface of the liquid transport element being in fluid communication with the reservoir and in fluid communication with the electric resistance heating element; and
  a secondary liquid transport element interposed in a flow path between the reservoir and the nonfibrous liquid transport element and overlying at least a portion of the microtextured surface of the nonfibrous liquid transport element, wherein the nonfibrous liquid transport element comprises at least one aperture therethrough and at least a portion of the secondary liquid transport element passes through the at least one aperture.

2. The aerosol delivery device of claim 1, wherein the nonfibrous liquid transport element is plate-shaped.

3. The aerosol delivery device of claim 1, further comprising a positive electric terminal engaged with a first portion of the pattern through an aperture and a negative electric terminal engaged with a second portion of the pattern through an aperture such that an electric current can be passed from terminal to terminal.

4. The aerosol delivery device of claim 1, further comprising a secondary liquid transport element interposed in a flow path between the reservoir and the nonfibrous liquid transport element and wherein the secondary liquid transport element is in fluid communication with the reservoir and in fluid communication with at least a portion of the nonfibrous liquid transport element.

5. The aerosol delivery device of claim 4, wherein the microtextured surface of the nonfibrous liquid transport element comprises a heating zone that includes the electrical resistance heating element and a second zone in spaced relation from the electrical resistance heating element, and wherein the secondary liquid transport element is in fluid communication with at least a portion of the second zone such that a flow path for the liquid aerosol precursor composition is established from the secondary liquid transport element to the second zone and from the second zone to the heating zone across the microtextured surface.

6. The aerosol delivery device of claim 5, wherein the nonfibrous liquid transport element is plate-shaped with a peripheral edge surrounding a central region, and wherein the second zone is located proximal to the peripheral edge and the heating zone comprises at least a portion of the central region.

7. The aerosol delivery device of claim 4, wherein the secondary liquid transport element comprises a fibrous material or ceramic material.

8. The aerosol delivery device of claim 4, wherein the secondary liquid transport element is overlying at least a portion of the microtextured surface.

9. The aerosol delivery device of claim 1, wherein the pattern on the microtextured surface comprises one or more straight or curvilinear elements extending from a first end to a second end.

10. The aerosol delivery device of claim 1, wherein the reservoir and atomizer are housed in a cartridge adapted for attachment to a control body, the control body comprising an electrical power source configured to provide electrical current flow to the electrical resistance heating element.

11. The aerosol delivery device of claim 1, further comprising one or more of:
  (a) an electrical power source configured to provide electrical current flow to the electrical resistance heating element;
  (b) a controller adapted for controlling electrical current flow from the electrical power source; and
  (c) a flow sensor in communication with the controller and adapted to sense a pressure drop within the aerosol delivery device or a portion thereof.

12. The aerosol delivery device of claim 1, wherein the pattern of the electrical resistance heating element is etched, printed, or adhered to the microtextured surface of the nonfibrous liquid transport element to physically combine the electrical resistance heating element and the nonfibrous liquid transport element.

13. The aerosol delivery device of claim 12, wherein the electrical resistance heating element is in the form of a conductive ink printed on the microtextured surface of the nonfibrous liquid transport element.

14. The aerosol delivery device of claim 1, wherein the protective layer is limited to a portion of the microtextured surface of the nonfibrous liquid transport element where the heating element is present.

* * * * *